United States Patent
de Muinck et al.

(10) Patent No.: US 9,233,137 B2
(45) Date of Patent: Jan. 12, 2016

(54) DENDRITIC CELL MODULATION IN POST-ISCHEMIC WOUNDS

(75) Inventors: Ebo D. de Muinck, Hanover, NH (US); Jose R. Conejo-Garcia, East Thetford, VT (US)

(73) Assignee: Celdara Medical, LLC, Lebanon, NH (US)

( * ) Notice: Subject to any disclaimer, the term of this patent is extended or adjusted under 35 U.S.C. 154(b) by 575 days.

(21) Appl. No.: 13/128,004

(22) PCT Filed: Nov. 6, 2009

(86) PCT No.: PCT/US2009/005995
§ 371 (c)(1),
(2), (4) Date: Nov. 1, 2011

(87) PCT Pub. No.: WO2010/053561
PCT Pub. Date: May 14, 2010

(65) Prior Publication Data
US 2012/0039985 A1    Feb. 16, 2012

Related U.S. Application Data

(60) Provisional application No. 61/112,375, filed on Nov. 7, 2008.

(51) Int. Cl.
*A61K 39/00*    (2006.01)
*A61K 35/15*    (2015.01)
*A61K 38/16*    (2006.01)
*A61K 38/47*    (2006.01)

(52) U.S. Cl.
CPC ............ *A61K 38/164* (2013.01); *A61K 38/168* (2013.01); *A61K 38/47* (2013.01)

(58) Field of Classification Search
None
See application file for complete search history.

(56) References Cited

U.S. PATENT DOCUMENTS

| | | |
|---|---|---|
| 2004/0213761 A1 | 10/2004 | Bowman et al. |
| 2004/0258670 A1 | 12/2004 | Laughlin et al. |
| 2004/0258688 A1 | 12/2004 | Hawiger et al. |
| 2006/0222633 A1 | 10/2006 | Shlomchik et al. |
| 2007/0065415 A1 | 3/2007 | Kleinsek et al. |
| 2008/0025913 A1 | 1/2008 | Bowdish et al. |

FOREIGN PATENT DOCUMENTS

| | | | |
|---|---|---|---|
| WO | WO 03/075953 | * | 9/2003 |
| WO | WO 03/078569 | * | 9/2003 |
| WO | WO 03/087021 A2 | | 10/2003 |
| WO | WO 2008/036374 A2 | | 3/2008 |

OTHER PUBLICATIONS

Fogoros RN (Coronary artery disease—An Overview, About.com Guide, pp. 1-2, updated Dec. 29, 2005) [retrieved on Jul. 15, 2013]. Retrieved from the Internet:<URL: http://heartdisease.about.com/od/coronaryarterydisease/a/CADoverview.htm>.*
Lu et al (AAPS Jour 8: E466-E478, 2006).*
Nanoparticle (from Wikipedia) http://en.wikipedia.org/wiki/Nanoparticle (pp. 1-9) Downloaded on May 20, 2014.*
Maekawa, Yuichiro, et al. "Survival and Cardiac Remodeling After Myocardial Infarction Are Critically Dependent on the Host Innate Immune Interleukin-1 Receptor-Associated Kinase-4 Signaling: A Regulator of Bone Marrow-Derived Dendritic Cells." *Circulation* (published online Sep. 21, 2009) 120:1401-1414.

* cited by examiner

*Primary Examiner* — Daniel E Kolker
*Assistant Examiner* — Aditi Dutt
(74) *Attorney, Agent, or Firm* — Wolf, Greenfield & Sacks, P.C.

(57) ABSTRACT

Compositions and methods useful for targeted depletion or modulation of dendritic cells are provided. The compositions and methods can be used to promote healing of ischemia-related injury, including ischemia-reperfusion injury. Disclosed are a variety of dendritic cell-targeted toxins, bone morphogenetic protein 7 (BMP7) agonists, and dendritic cell-targeted transforming growth factor beta 1 (TGF-β1) antagonists, all useful in practicing methods of the invention. The inventive compositions and methods can be used in the treatment of various conditions including myocardial infarction, stroke, and critical limb ischemia.

26 Claims, 5 Drawing Sheets

DENDRITIC CELL MODULATION IN POST-ISCHEMIC WOUNDS

RELATED APPLICATIONS

This application is a national stage filing under 35 U.S.C. §371 of international application PCT/US2009/005995, filed Nov. 6, 2009 designating the United States of America. This application claims the benefit of U.S. provisional application No. 61/112,375, filed on Nov. 7, 2008. The entire teachings of the referenced provisional application are incorporated by reference herein.

GOVERNMENT SUPPORT

This invention was made with government support under grant R01 HL078622 awarded by the National Institutes of Health. The government has certain rights in the invention.

BACKGROUND OF THE INVENTION

Interruption of an organ's blood flow, with its subsequent lack of oxygen and nutrient supply, is only part of ischemia-related tissue injury. Once the blood flow and oxygen supply are reestablished, reperfusion enhances the injury caused by the ischemic period, aggravating the damage caused at the cellular level. This phenomenon, known as ischemia-reperfusion injury, directly impacts tissue viability.

During an ischemic period, several functional changes occur at the cellular level that promote cell injury. A decrease in oxidative phosphorylation results in ATP depletion and derangements in calcium homeostasis. The deleterious effects of ATP depletion are further enhanced by the production of several substances, including reactive oxygen species (ROS), cytokines, adhesion molecules, and vasoactive agents (endothelin and thromboxane-A2). Factors most frequently implicated in ischemia-reperfusion injury are TNF-α, interleukin 1 (IL-1) and interleukin 6 (IL-6), prostaglandins (PG), and ROS, especially superoxide ($O_2^-$) and hydrogen peroxide ($H_2O_2$). During reperfusion, tumor necrosis factor alpha (TNF-α) and other mediators activate many of the proteins involved in apoptosis, such as the proteases caspase-3 and caspase-8, along with mitochondria cytochrome-C release to the cytoplasm.

These alterations are accompanied by a decrease of cytoprotective substances including nitric oxide (NO) and prostacyclin. NO is synthesized from L-arginine by the action of nitric oxide synthase (NOS). NO is an important mediator of immunomodulation, neurotransmission, and platelet aggregation. Within endothelial cells, NO triggers cGMP to reduce vascular tone and act as a vasodilator. NO can mediate the intensity of the ischemia-reperfusion injury by modulating neutrophil adhesion, platelet aggregation, and vasoconstriction. The balance between vasorelaxation and vasoconstriction is affected by the balance between endothelin (ET) and NO. Therefore, one of the mechanisms involved in ischemia-reperfusion injury is loss of the equilibrium between ET and NO levels during reperfusion. At the beginning of reperfusion, NO levels decrease and ET levels increase, favoring microcirculatory vasoconstriction.

Ischemia ultimately leads to cell death if not resolved by reperfusion. Studies by Reimer and Jennings and colleagues laid the foundation for early reperfusion as the definitive approach to treat acute myocardial infarction. Reimer et al. (1977) *Circulation* 56:786-794. The study by DeWood et al. (1980)*N. Engl. J. Med.* 303:897-902, demonstrating that acute myocardial infarction was largely an occlusive event of sudden onset, due to thrombus formation in the affected coronary artery, set the stage for thrombolysis as an approach to restore reflow to the infarct-related artery. Infarct size reduction is an important therapeutic goal since it is linked to other short- and long-term outcomes such as arrhythmias, mortality, and loss of productivity. In addition, the size of the infarct is related to the incidence and severity of heart failure. Therefore, it is important to salvage as much myocardium as possible, historically by initiating reperfusion as rapidly as possible.

While the majority of therapeutic approaches for treatment of acute evolving myocardial infarction have been designed to reduce the duration and severity of ischemia; newer generation approaches target reperfusion injury. Various approaches have been taken to attenuate reperfusion injury, including the systemic or local infusion of adenosine, nitric oxide, oxygen radical scavengers, anti-inflammatory agents, and the filtration of inflammatory cells at the time of reperfusion.

SUMMARY OF THE INVENTION

The invention is based at least in part on the surprising discovery by the inventors that temporary dendritic cell (DC)-specific depletion or functional modulation of DCs can reduce post-ischemic tissue necrosis and promote post-ischemic tissue function recovery following an ischemia-reperfusion event. The invention provides DC-targeted compositions and methods useful for reducing post-ischemic tissue necrosis and promoting post-ischemic tissue function recovery following an ischemia-reperfusion event. The invention is useful, either alone or as an adjunct to other therapies useful in the treatment of ischemia-related conditions, for treating any number of such conditions, including but not limited to acute myocardial infarction, stroke, and critical limb ischemia.

Thus far, the most effective method to reduce myocardial infarction (MI) size has been to re-establish blood flow in the infarct-related artery. The invention is further based at least in part on the surprising discovery by the inventors that in the absence of reperfusion, a significant reduction in MI size and a significant improvement in residual left ventricle (LV) function can be achieved through temporary depletion of DC. Accordingly, when DC depletion is combined with reperfusion therapy, the combined effect will result in a greater reduction of MI size and better preservation of LV function than reperfusion therapy alone.

Ischemia-reperfusion injury contributes to development of post-ischemic wounds by mechanisms that include both microvascular vasoconstriction and inflammatory and other immune-mediated tissue injury.

A number of studies have established that systemic, broad-spectrum immune suppression, for example the use of glucocorticoids, increases the risk of myocardial rupture following myocardial infarction. Accordingly, such approaches are generally considered to be contraindicated.

In contrast, the present invention involves highly selective DC depletion and/or DC suppression for use in ameliorating chronic ischemia and ischemia-reperfusion injury and in promoting post-ischemic wound healing.

The methods of the invention involve the temporary depletion or functional modulation of DCs in the setting of a post-ischemic wound. It has surprisingly been discovered that depletion or functional modulation of DCs for even as little as one day can improve post-ischemic wound healing. The invention also contemplates longer periods of depletion or functional modulation of DCs, for example at least one week, at least two weeks, at least one month, and at least two months.

The depletion of functional modulation of DCs can begin at any time within six months of the onset of the ischemic wound. In one embodiment the depletion or modulation is started within one day of the onset or diagnosis of the ischemic wound. In one embodiment the depletion or modulation is started within one week of the onset or diagnosis of the ischemic wound. In one embodiment the depletion or modulation is started within one month of the onset or diagnosis of the ischemic wound.

DC depletion or functional modulation can be accomplished by a single period of DC-depletion or DC-modulation as disclosed herein. Alternatively, depletion or functional modulation can be accomplished by multiple periods of DC-depletion or DC-modulation agent as disclosed herein, for example by alternating periods of administration with periods without administration. In one embodiment intermittent depletion or functional modulation of DCs is applied over an extended period, for example, over a period of months.

As disclosed herein, $CD11c^+$ DC, a subpopulation of myeloid cells, contributes significantly to myocardial infarction (MI) wound healing and acquire endothelial markers in the MI wound. These cells, which are characterized by the co-expression of both leukocyte and endothelial markers, are deemed to be vascular leukocytes (VLC). Also as disclosed herein, temporary depletion of $CD11c^+$ DC during MI wound healing significantly reduces MI size and significantly preserves left ventricular function.

The invention in one aspect is a method of promoting post-ischemic wound healing in a subject. The method includes the step of administering to a subject having a post-ischemic wound a dendritic cell (DC)-targeted cell-depleting agent in an amount effective to deplete DCs in the post-ischemic wound, thereby promoting post-ischemic wound healing.

The invention in one aspect is a method of promoting post-ischemic wound healing in a subject. The method includes the step of administering to a subject having a post-ischemic wound a dendritic cell (DC)-targeted cell-depleting agent in an amount effective to reduce tissue necrosis in the post-ischemic wound, thereby promoting post-ischemic wound healing.

In each of the foregoing aspects of the invention, in one embodiment the DC-targeted cell-depleting agent comprises a toxin that kills DCs.

In each of the foregoing aspects of the invention, in one embodiment the toxin is selected from diphtheria toxin (DT), *Pseudomonas* exotoxin A (PEA), ricin, saporin, gelonin, and enzymatically active fragments thereof.

In each of the foregoing aspects of the invention, in one embodiment the DC-targeted cell-depleting agent comprises an antibody, or at least an antigen-binding portion thereof, that binds to a DC surface marker.

In each of the foregoing aspects of the invention, in one embodiment the DC-targeted cell-depleting agent is an immunotoxin.

In each of the foregoing aspects of the invention, in one embodiment the DC-targeted cell-depleting agent is formulated as a nanoparticle.

In each of the foregoing aspects of the invention, in one embodiment the DC-targeted cell-depleting agent is formulated as a liposome or plasma membrane vesicle.

The invention in one aspect is a method of promoting post-ischemic wound healing in a subject. The method includes the step of administering to a subject having a post-ischemic wound a dendritic cell (DC)-targeted bone morphogenetic protein 7 (BMP7) agonist in an amount effective to increase BMP7 release by DCs in the post-ischemic wound, thereby promoting post-ischemic wound healing.

In one embodiment the DC-targeted BMP7 agonist comprises an antibody, or at least an antigen-binding portion thereof, that binds to a DC surface marker.

In one embodiment the DC-targeted BMP7 agonist is formulated as a nanoparticle.

In one embodiment the DC-targeted BMP7 agonist is formulated as a liposome or plasma membrane vesicle.

The invention in one aspect is a method of promoting post-ischemic wound healing in a subject, comprising administering to a subject having a post-ischemic wound a dendritic cell (DC)-targeted transforming growth factor beta 1 (TGF-β1) antagonist in an amount effective to reduce TGF-β1 release by DCs in the post-ischemic wound, thereby promoting post-ischemic wound healing.

In one embodiment the DC-targeted TGF-β1 antagonist comprises an antibody, or at least an antigen-binding portion thereof, that binds to a DC surface marker.

In one embodiment the DC-targeted TGF-β1 antagonist is formulated as a nanoparticle.

In one embodiment the DC-targeted TGF-β1 antagonist is formulated as a liposome or plasma membrane vesicle.

In each of the foregoing aspects of the invention, in one embodiment the DC surface marker is selected from CD11c, CD205, CD206, and CD209.

In each of the foregoing aspects of the invention, in one embodiment the DC surface marker is CD205.

In each of the foregoing aspects of the invention, in one embodiment the post-ischemic wound is an acute myocardial infarction.

In each of the foregoing aspects of the invention, in one embodiment the post-ischemic wound is a stroke.

In each of the foregoing aspects of the invention, in one embodiment the post-ischemic wound is critical limb ischemia.

In each of the foregoing aspects of the invention, in one embodiment the subject is a human.

DETAILED DESCRIPTION OF THE INVENTION

Figure 1A:
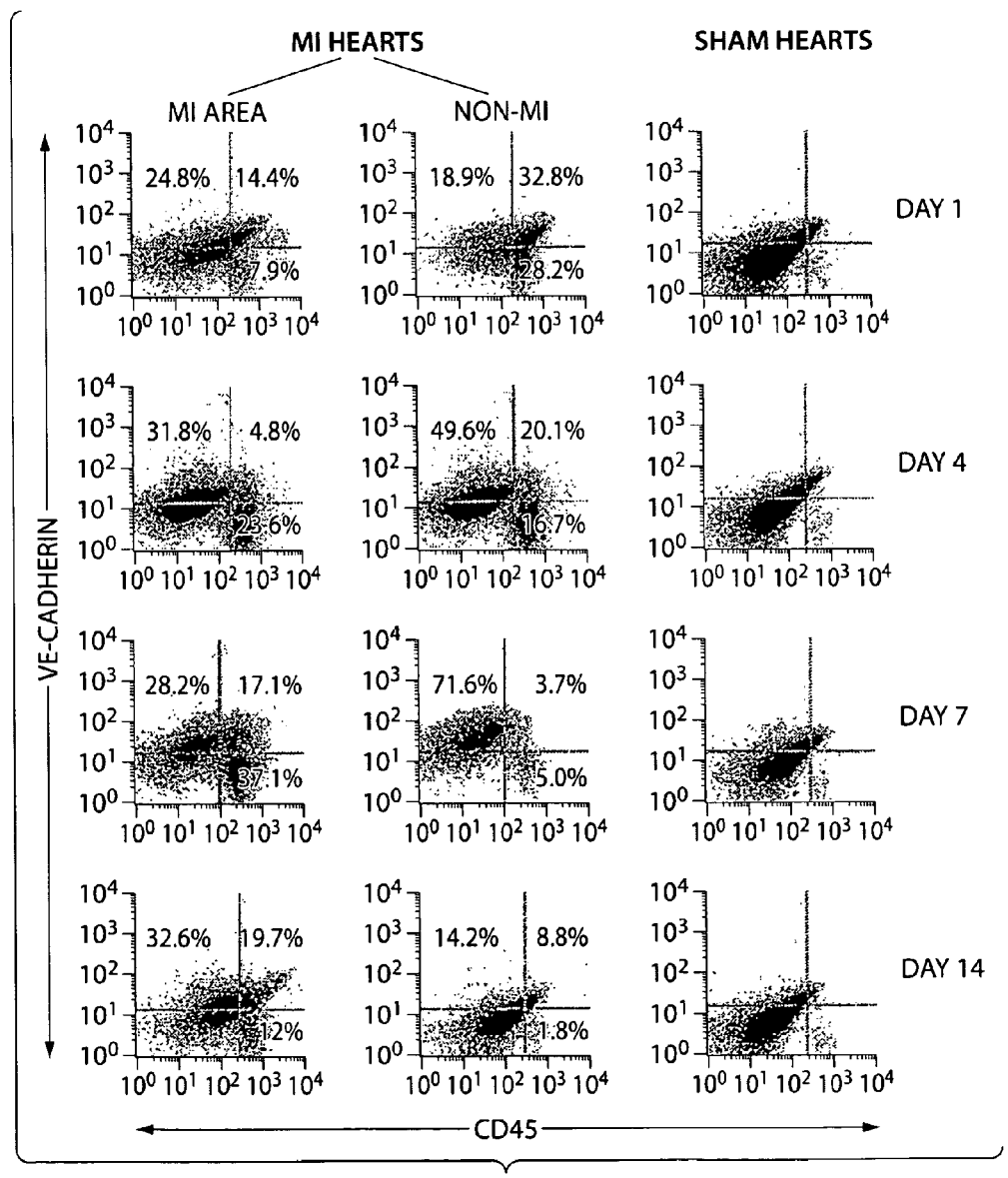
FIG. 1 is a series of graphs depicting results of fluorescence-activated cell sorting analysis at different time points after induction of myocardial infarction (MI). Panel A shows that leukocytes that express the endothelial marker VE-cadherin first appear in the non-infarcted segment of the heart after MI and then reach their maximum at seven days post-MI. Panel B depicts how a percentage of VLC expresses the myeloid marker CD13/APN and the dendritic cell marker CD11c. Panel C shows that VLC first reach a peak in the viable area of the infarcted heart and then appear in the infarcted segment. Sham operated animals show no increase in VLC.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The invention in at least one aspect is a method of promoting post-ischemic wound healing in a subject. As used herein, "promoting" refers to inducing, increasing, or both inducing and increasing, as compared to a suitable control. A suitable control can be a subject that is similarly in need of post-ischemic wound healing but does not receive a compound or treatment of the invention. In one embodiment a suitable control is a historical control. In one embodiment a suitable control is a suitable control population.

As used herein, a "post-ischemic wound" refers to any tissue that has suffered or is at risk of suffering ischemia-reperfusion injury. In one embodiment a "post-ischemic wound" refers to any tissue that has suffered ischemia-reperfusion injury. In one embodiment post-ischemic wound" refers to any tissue that is at risk of suffering ischemia-reperfusion injury. Tissue that is at risk of suffering ischemia-reperfusion injury can be tissue that shares at least one vascular supply in common with tissue that has suffered ischemia-reperfusion injury. Typically such tissue at risk of suffering ischemia-reperfusion injury is in the vicinity of or adjacent to tissue that has suffered ischemia-reperfusion injury. In one embodiment tissue at risk of suffering ischemia-reperfusion injury is, from an arterial supply perspective, proximal to tissue that has suffered ischemia-reperfusion injury. In one embodiment tissue at risk of suffering ischemia-reperfusion injury is, from an arterial supply perspective, distal to tissue that has suffered ischemia-reperfusion injury.

As used herein, "post-ischemic wound healing" refers to the extent of structural, functional, or both structural and functional recovery of a post-ischemic wound. As healing takes place over time, in one embodiment "post-ischemic wound healing" refers to the extent of structural, functional, or both structural and functional recovery of a post-ischemic wound at a given time. For similar reasons, in one embodiment "post-ischemic wound healing" refers to the ultimate extent of structural, functional, or both structural and functional recovery of a post-ischemic wound.

A "subject" as used herein refers to a living mammal. In one embodiment a subject is a living non-human mammal. In one embodiment a subject is a living human.

A "subject having a post-ischemic wound" is a subject that has at least one objective manifestation of a post-ischemic wound. In various embodiments such a subject is a subject with an acute ischemic injury to brain, spinal cord, peripheral nerve, eye, heart, lung, gall bladder, liver, pancreas, kidney, stomach, small intestine, large intestine, ovary, testis, limb, skeletal muscle, or any combination thereof. In one embodiment such a subject is a subject with an acute MI. In one embodiment such a subject is a subject with cerebral ischemia, e.g., stroke or cerebral infarction. In one embodiment a subject is a subject with critical limb ischemia. In one embodiment a subject is a recipient of a tissue or organ transplant, where the graft tissue or organ has been deprived of blood flow for at least four minutes prior to, during, and/or following harvest. An objective manifestation of a post-ischemic wound can include at least one of a change in function, change in tissue structure, and change in expression or release of a measurable marker that is consistent with a post-ischemic wound.

As used herein, the term "critical limb ischemia" (CLI) refers to a condition characterized by chronic ischemic at-rest pain, ulcers, or gangrene in one or both legs attributable to objectively proven arterial occlusive disease. Critical limb ischemia implies chronicity and is to be distinguished from acute limb ischemia. Its incidence is approximately 500 to 1000 per million year, with the highest rates among older subjects, smokers and diabetics. The rate of primary amputation ranges from 10% to 40%. Patients with critical limb ischemia have an elevated risk of future myocardial infarction, stroke and vascular death, 3-fold higher than patients with intermittent claudication. Due to its negative impact on the quality of life and the poor prognosis both in terms of limb salvage and survival, critical limb ischemia is a critical public health issue.

For patients suffering from high-grade stenoses or short arterial occlusions, percutaneous transluminal angioplasty (PTA) is typically recommended as the first form of treatment. Surgical procedures—preferably endovascular techniques—are second on the list, offering patients a lower morbidity and mortality risk compared to open surgical revascularizations. Approximately 20-30% of CLI patients are not considered candidates for vascular or endovascular procedures. In those patients where amputation is not required and vascular reperfusion is not possible when using thrombolysis, angioplasty, or surgical reconstruction, medical treatment to improve microcirculatory blood flow is considered.

Thus beyond acute ischemic events, depletion of DCs in chronic or at least long-term ischemic injury is also beneficial. DC depletion following an ischemic event reduces markers of inflammation and anti-angiogenic factors and promotes wound healing in the setting of CLI.

Obesity leads to decreased insulin sensitivity, which in turn leads to hyperglycemia. Reduced insulin sensitivity and hyperglycemia are risk factors for the development of CLI because they impair neo-vascularization which can protect against CLI. Once patients have reached the stage of CLI, reduced insulin sensitivity and hyperglycemia have a negative impact on wound healing. In addition to its potent anti-inflammatory effect, DC depletion restores insulin sensitivity, thereby reducing the risk for the development of CLI and improving wound healing once CLI has ensued. That DC depletion restores insulin sensitivity is of extreme significance in view of the epidemic of obesity and concomitant reduced insulin sensitivity that is currently spreading throughout industrialized society.

As used herein, a "dendritic cell" refers to a circulating bone marrow-derived immune accessory cell that can function as an antigen-presenting cell, including myeloid DCs, plasmacytoid DCs, and precursors thereof. DCs have a complex biology that includes morphological and phenotypic changes in going from precursor to mature DCs and in going from naive to antigen-activated DCs. Myeloid DCs are classical DCs that were first identified by their ability to stimulate T-cell responses. They can be cultured from monocytes and are considerably more numerous than plasmacytoid DCs. Plasmacytoid DCs resemble plasma cells and acquire DC morphology only upon activation. Immature DC function principally to capture antigen, whereupon they undergo maturation and then function principally to present processed antigen to T cells. DCs express a number of surface markers, including but not limited to CD11c. For example, $CD8^-$ myeloid DCs are strongly $CD11c^+$ and $CD11b^+$, whereas plasmacytoid DCs are relatively weakly $CD11c^+$ and $CD11b^-$. Additional surface markers characteristic of DCs are discussed below. In one embodiment a "dendritic cell" is a $CD11c^+$ DC.

As used herein, a "dendritic cell-targeted cell-depleting agent" is an agent that is capable of selectively killing DCs or is capable of selectively incapacitating DCs such that the DCs are non-functional. In one embodiment a "dendritic cell-targeted cell-depleting agent" is an agent that is capable of selectively killing DCs. An agent that is capable of selectively killing DCs does not kill significant numbers of cells other than DCs when used in accordance with the invention. In one embodiment a "dendritic cell-targeted cell depleting agent" is an agent that is capable of selectively killing myeloid DCs, plasmacytoid DCs, and precursors thereof. In one embodiment a "dendritic cell-targeted cell depleting agent" is an agent that is capable of selectively killing $CD11c^+$ DCs or is capable of selectively incapacitating $CD11c^+$ DCs such that the $CD11c^+$ DCs are non-functional.

In one embodiment a "dendritic cell-targeted cell depleting agent" is an agent that is capable of selectively killing $CD11c^+$ DCs.

The invention in one embodiment entails administering to a subject having a post-ischemic wound a dendritic cell-targeted cell-depleting agent in an amount effective to deplete DCs in the post-ischemic wound. The administering can be by any suitable route to bring the DC-targeted cell-depleting agent into contact with DCs. Administering will generally include intravascular administering. For example, in one embodiment the administering can be systemic by intravenous administration. Systemic administration of the DC-targeted cell-depleting agent will deplete circulating DCs as well as interstitial DCs, that is, DCs wherever they exist in the body. Accordingly, systemic administration of the DC-targeted cell-depleting agent will effect both generalized depletion of DCs as well as depletion of DCs in the post-ischemic wound. Such systemic administration can accomplished by one or more bolus injections, or by infusion, or by any combination thereof.

Alternatively or in addition to systemic administration, in one embodiment the DC-targeted cell-depleting agent is administered locally, for example by intracoronary injection, myocardial injection, pericardial injection, epicardial injection, or retrovenous injection. Local administration of the DC-targeted cell-depleting agent will preferentially deplete interstitial DCs, that is, DCs in the post-ischemic wound. Such local administration can accomplished by one or more bolus injections, or by infusion, or by any combination thereof.

The administering, whether local, systemic, or a combination of local and systemic, will generally be short-term, i.e., for a duration sufficient to effect at least 10 percent DC depletion for one to fourteen days as compared to untreated control. In various embodiments the administering will be for a duration sufficient to effect at least 10 percent DC depletion for 1, 2, 3, 4, 5, 6, 7, 8, 9, 10, 11, 12, 13, or 14 days. In one embodiment the administering will be for a duration sufficient to effect at least 10 percent DC depletion for up to 30 days.

The administering results in depletion of DCs in the post-ischemic wound. DC depletion in the post-ischemic wound can be measured directly or indirectly using any suitable method for detecting viable DCs. For example, DC depletion in the post-ischemic wound can be measured by analysis of a tissue or blood sample, obtained from a treated subject, for the presence of cells bearing DC surface markers or features and comparing the measured result to a suitable control. For example, in one embodiment the measurement can be accomplished by fluorescence-activated cell sorting (FACS) analysis of peripheral blood mononuclear cells (PBMC) with staining provided by a suitable labeled anti-CD11c antibody. In one embodiment the measurement can be accomplished by immunohistochemical staining with a suitable labeled anti-CD11c antibody. In one embodiment the measurement can be accomplished by histologic examination using light or electron microscopy.

The depletion can but need not necessarily be complete depletion. In various embodiments the depletion is at least 10 percent, at least 20 percent, at least 30 percent, at least 40 percent, at least 50 percent, at least 60 percent, at least 70 percent, at least 80 percent, or at least 90 percent. In one embodiment the depletion is essentially 100 percent. For example, if DCs normally represent 5 percent of all PBMC, and if DCs in a treated subject represent 0.5 percent of all PBMC, then there is a 90 percent depletion of all circulating DCs in the treated subject. Such 90 percent depletion of all circulating DCs in the treated subject is expected to be accompanied by a 90 percent depletion of all DCs in the post-ischemic wound.

As DCs in a post-ischemic wound normally can vary as a function of time, for example as measured from an acute event, the depletion can accordingly be measured in terms of comparison to a control amount of DCs in a post-ischemic wound at a given time.

In one embodiment the DC-targeted cell-depleting agent is administered in an amount effective to deplete DCs in the post-ischemic wound. As used herein, an "effective amount" is any amount that is sufficient to achieve a desired biological result. For example, an amount effective to deplete DCs in the post-ischemic wound is any amount that is sufficient to deplete DCs in the post-ischemic wound. As noted above, in one embodiment depletion of DCs in the post-ischemic wound can be inferred from depletion of DCs in PBMC.

In one embodiment the DC-targeted cell-depleting agent is administered in an amount effective to reduce tissue necrosis in the post-ischemic wound. As used herein, "necrosis" refers to cell death. Necrosis also refers to the morphological changes indicative of cell death caused by enzymatic degradation, as is well known by persons skilled in the art. As used herein, "necrosis" in one embodiment can include apoptotic cell death. The presence of tissue necrosis can be determined by any suitable method, including gross inspection, histology, functional assessment, detection of release of intracellular proteins and enzymes such as troponins, lactate dehydrogenase, creatine kinase, aspartate aminotransferase, and any combination thereof. Such methods for detecting necrosis are well known in the art and need not be described in greater detail here. In the context of myocardial infarction, functional assessment can include, for example, local wall motion abnormality, MRI assessment, radionuclide scanning, echocardiography, and left ventricle angiography.

The reduction of necrosis is at least a detectable reduction as compared to a suitable control. The reduction can but need not necessarily be complete reduction. In various embodiments the reduction is at least 10 percent, at least 20 percent, at least 30 percent, at least 40 percent, at least 50 percent, at least 60 percent, at least 70 percent, at least 80 percent, or at least 90 percent as compared to a suitable control. In one embodiment the reduction is essentially 100 percent.

As necrosis can vary as a function of time, for example as measured from an acute event, the reduction of necrosis can accordingly be measured in terms of comparison to a control amount of necrosis at a given time.

In certain embodiments the DC-targeted cell-depleting agent includes an antibody, or at least an antigen-binding portion thereof, that binds to a DC surface marker. As used herein, a "DC surface marker" refers to any molecule that is characteristically expressed on the surface of a DC. In one embodiment a "DC surface marker" refers to any molecule that is exclusively expressed on the surface of a DC. In some embodiments a DC surface marker is capable of being internalized by the DC, such that the marker can deliver a molecule that binds to the marker to the interior of the DC. Since some of the characteristic functions of DC are to capture, internalize, process, and present antigen, DC are known to express markers that internalize molecules that bind to them.

In one embodiment the DC surface marker is CD11c, CD205, CD206, CD209, or any combination thereof. In one embodiment the DC surface marker is CD11c.

CD11c is a 150 kDa type I transmembrane protein also known as Integrin, alpha X (complement component 3 receptor 4 subunit) (ITGAX), and p150/95. This protein combines with the beta 2 chain (ITGB2) to form a leukocyte-specific integrin referred to as CD11a/CD18 or inactivated-C3b (iC3b) complement receptor 4 (CR4). Antibodies specific for human and mouse CD11c are commercially available from Becton Dickinson (San Jose, Calif.) and Abcam Inc. (Cambridge, Mass.), respectively. A cDNA sequence for human CD11c is available as GenBank accession no. NM_000887, and a corresponding amino acid sequence is available as GenBank accession no. NP_000878. A cDNA sequence for murine CD11c is available as GenBank accession no. NM_021334, and a corresponding amino acid sequence is available as GenBank accession no. NP_067309.

CD205 is a 205 kDa integral membrane glycoprotein also known as DEC205 and DEC-205 (dendritic and epithelial cells, 205 kDa). Inaba et al. (1995) *Cell. Immun.* 163: 148-156; Witmer-Pack et al. (1995) *Cell. Immun.* 163: 157-162. This membrane protein is homologous to the macrophage mannose receptor and acts as an endocytic receptor and thereby mediates efficient processing and presentation of antigens in vivo, leading to the induction of T cell immunity or tolerance. Bonifaz et al. (2002) *J. Exp. Med.* 196: 1627-1638. CD205 is expressed at high levels on mouse dendritic cells (DCs) in the skin (Langerhans cells), on DCs residing in the T-cell areas of peripheral lymphoid organs, and on DCs generated in vitro from bone marrow progenitors. Kraal et al. (1986) *J. Exp. Med.* 163: 981-997. To a much lower extent, CD205 is also expressed on mature B cells, granulocytes, and T cells. Antibodies specific for human and mouse CD205 are commercially available from eBioscience Inc. (San Diego, Calif.) and Miltenyi Biotec Inc. (Auburn, Calif.), respectively. A cDNA sequence for human CD205 is available as GenBank accession no. AY682091, and a corresponding amino acid sequence is available as GenBank accession no. AAT85634.

CD206 is a 175 kDa transmembrane glycoprotein also known as mannose receptor (MR). This membrane protein is a pattern recognition receptor that is classified as a member of the vertebrate C-type lectin receptor family. It is expressed on monocytes and dendritic cells and is believed to be involved in both innate and adaptive immunity in response to bacteria, yeasts, mycobacteria, and parasites. Zamze et al. (2002) *J. Biol. Chem.* 277:41613. Antibodies specific for human CD206 are commercially available, for example, from Hycult Biotechnology (Uden, The Netherlands). A cDNA sequence for human CD206 is available as GenBank accession no. NM_002438, and a corresponding amino acid sequence is available as GenBank accession no. NP_002429.

CD209 is a 44 kDa type II transmembrane glycoprotein also known as DC-SIGN, DC-SIGN1, DCSIGN, and CLEC4L. This membrane protein is a pattern recognition receptor that is classified as a member of the vertebrate C-type lectin receptor family. It is expressed on monocytes and dendritic cells and is believed to be involved in both innate and adaptive immunity in response to viruses, bacteria, and fungi. Geijtenbeek et al. (2002). *J. Leukoc. Biol.* 71:921-31. Human dendritic cells preferentially express DC-SIGN. It has been postulated that DC-SIGN serves as a receptor for capture, trafficking, and transmission of human immunodeficiency virus (HIV) to T cells and supports primary immune response. Antibodies specific for human CD209 are commercially available from eBioscience Inc. (San Diego, Calif.). A cDNA sequence for human CD209 is available as GenBank accession no. NM_021155, and a corresponding amino acid sequence is available as GenBank accession no. NP_066978.

As used herein, the term "antibody" refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies typically comprise tetramers of protein molecules which form an immunoglobulin molecule. The antibodies in the present invention may exist in a variety of forms including, for example, polyclonal antibodies, monoclonal antibodies, Fv, Fab and F(ab)$_2$, as well as single chain antibodies and humanized antibodies. Harlow et al. (1988) *Antibodies: A Laboratory Manual*, Cold Spring Harbor, N.Y.; Houston et al. (1988) *Proc. Natl. Acad. Sci. USA* 85:5879-5883; Bird et al. (1988) *Science* 242:423-426.

Antibodies include polyclonal and monoclonal antibodies, as well as antigen-binding fragments thereof. The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as originally described in 1975 by Kohler and Milstein (*Nature* 256:495-7) as well as those described; for example, in Harlow et al. (1988, In: Antibodies, A Laboratory Manual, Cold Spring Harbor, N.Y.) and in Tuszynski et al. (1988) *Blood* 72:109-115. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992) *Critical Rev. Immunol.* 12:125-168) and the references cited therein. Further, the antibody of the invention can be "humanized" using the technology first described by Riechmann et al. (1988) *Nature* 332:323-7.

To generate a phage antibody library, a cDNA library is first obtained from mRNA which is isolated from cells, e.g., spleen cells or a hybridoma, which cells express the desired protein to be expressed on the phage surface, e.g., the desired antibody. cDNA copies of the mRNA are produced using reverse transcriptase. cDNA which specifies immunoglobulin fragments are obtained by polymerase chain reaction (PCR) and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989) *Molecular Cloning: A Laboratory Manual*, Cold Spring Harbor, N.Y.

Bacteriophage which encodes the desired antibody, may be engineered such that the protein is displayed on the surface thereof in such a manner that it is available for binding to its corresponding binding protein, e.g., the antigen against which the antibody is directed. Thus, when bacteriophage which expresses a specific antibody is incubated in the presence of a cell which expresses the corresponding antigen, the bacteriophage will bind to the cell. Bacteriophage which does not express the antibody will not bind to the cell. Such panning techniques are well known in the art and are described for example, in Wright et al. (supra).

Processes such as those described above have been developed for the production of human antibodies using M13 bacteriophage display. Burton et al. (1994) *Adv. Immunol.* 57:191-280. Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region (CH1) domain of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991) *J. Mol. Biol.* 222: 581-597. Panning of phage so generated for the isolation of a desired antibody is conducted in a manner similar to that described for phage libraries comprising Fab DNA.

Antibodies and antigen-binding portions thereof can be used to target DCs, for example to deliver a cell-depleting agent or other therapeutic agent to DCs, in accordance with the invention. In one embodiment the targeting antibodies or antigen-binding portions thereof are linked to a cell-depleting agent or other therapeutic agent, and conjugates so formed are used alone. In one embodiment the targeting antibodies or antigen-binding portions thereof are linked to a delivery vehicle such as a nanoparticle, liposome, or plasma membrane vesicle, which delivery vehicle is coated with or in which is encapsulated a cell-depleting agent or other therapeutic agent such as is disclosed herein.

As used herein, a "nanoparticle" refers to any biocompatible solid phase particulate substrate characterized by having a greatest dimension along any axis of 1 nm to 10,000 nm (10 μm). In one embodiment the nanoparticle is biodegradable. Solid-phase biodegradable nanoparticles can be manufactured from polymers including, but not limited to, biodegradagble poyesters, such as poly(lactic acid), poly(glycolic acid), and copolymers (including block copolymers) thereof, as well as block copolymers of poly(lactic acid) and poly(ethylene glycol); polyorthoesters such as polymers based on 3,9-diethylidene-2,4,8,10-tetraxaspiro[5,5]undecane (DETOSU); polyanhydrides such as poly(anhydride) polymers based on relatively hydrophilic monomers such as sebacic acid; polyanhydride imides, such as polyanhydride polymers based on sebacic acid-derived monomers incorporating amino acids such as glycine or alanine; polyanhdride esters; polyphosphazenes, especially polyphosphazenes which contain hydrolysis-sensitive ester groups which can catalyze degradation of the polymer backbone through generation of carboxylic acid groups; and polyamides such as poly(lactic acid-co-lysine).

In one embodiment the nanoparticle is non-biodegradable. A wide variety of nonbiodegradable materials suitable for manufacturing nanoparticles are known, including, but not limited to, polystyrene, polypropylene, polyethylene, latex, gold, and ferromagnetic or paramagnetic materials.

Nanoparticles can be loaded, on their surface, with one or more targeting and/or therapeutic agents using techniques known in the art.

As used herein, a "liposome" refers to a substantially hollow liquid phase carrier that is usually 10-200 μm in diameter. A liposome is a tiny bubble (vesicle), made out of phopholipids, similar to a cell membrane. Liposomes can be filled with drugs, and used to deliver drugs for cancer and other diseases. The lipids in the plasma membrane are chiefly phospholipids like phosphatidyl ethanolamine and cholesterol. Phospholipids are amphiphilic with the hydrocarbon tail of the molecule being hydrophobic; its polar head hydrophilic. As the plasma membrane faces watery solutions on both sides, its phospholipids accommodate this by forming a phospholipid bilayer with the hydrophobic tails facing each other.

Liposomes can be created by sonicating phospholipids in water. Low shear rates create multilamellar liposomes, which have many layers like an onion. Continued high-shear sonication tends to form smaller unilamellar liposomes. In this technique, the liposome contents are the same as the contents of the aqueous phase. Sonication is generally considered a "gross" method of preparation, and newer methods such as extrusion are employed to produce materials for human use.

Liposomes can be composed of naturally-derived phospholipids with mixed lipid chains (like egg phosphatidylethanolamine), or of pure surfactant components like dioleoylphosphatidylethanolamine (DOPE). Liposomes, usually but not by definition, contain a core of aqueous solution; lipid spheres that contain no aqueous material are called micelles, however, reverse micelles can be made to encompass an aqueous environment.

Liposomes can be loaded, on their surface, with one or more targeting and/or therapeutic agents using techniques known in the art. See, for example, US 2007/0026057 A1. Alternatively or in addition, liposomes can be loaded, in their interior, with one or more therapeutic agents using techniques known in the art.

In one embodiment a DC-targeting agent includes a toxin. As used herein, a "toxin" refers to an agent that is capable of adversely affecting a cell's viability or function, including in particular a DC. In one embodiment, a "toxin" refers to an agent that is capable of poisoning a cell, including in particular a DC. Toxins typically interfere with some key metabolic pathway in a cell so that cell brought into contact with the toxin dies. Toxins can include certain radioisotopes, small molecules, peptides, proteins, and certain inorganic species including cyanides, alkaloids, arsenic, mercury, beryllium, lead, cadmium, fluorine, chlorine, bromine, and various silver preparations. For example, in one embodiment a DC-targeting antibody or antigen-binding portion thereof is conjugated to a radiolabel that is capable of killing a cell. In one embodiment the radiolabel is $^{131}$I. DC-targeted delivery of an appropriate radiolabel is capable of selectively killing DCs.

In one embodiment the toxin is selected from diphtheria toxin (DT), *Pseudomonas* exotoxin A (PEA), ricin, saporin, gelonin, and enzymatically active fragments thereof.

Examples of suitable toxins and the methods of generating the same can be found in the following list of references. Levy et al. (1991) *J. Clin. Oncol.* 9:537-538; Burbage et al. (1997) *Leukemia Res.* 21:681690; Chandler et al. (1996) *Seminars Pediatric Surgery* 5:206-211; Collinson et al. (1994) *J. Immunopharmacol.* 16:37-49; Essand et al. (1998) *Internatl. J. Cancer* 77:123-127; Faguet et al. (1997) *Leukemia Lymphoma* 25:509-520; Flavell et al. (1995) *Brit. J. Cancer* 72:1373-1379; Frankel et al. (1997) *Leukemia Lymphoma* 26:287-298; Knowles et al. (1987) *Anal. Biochem.* 160:440-443; Kreitman et al. (1997) *Blood* 90:252-259; Lynch et al. (1997) *J. Clin. Oncol.* 15:723-734; Mansfield et al. (1997) *Blood* 90:2020-2026; Maurer-Gebhard et al. (1998) *Cancer Res.* 58:2661-2666; O'Toole et al. (1998) *Curr. Topics Microbiol. Immunol.* 234:35-56; Press et al. (1998) *Cancer Journal From Scientific American* 4:S19-S26; Przepiorka et al. (1995) *Bone Marrow Transplantation* 16:737-741; Schnell et al. (1996) *Internatl. J. Cancer* 66:526-531; Spyridonidis et al. (1998) *Blood* 91:1820-1827; Winkler et al. (1997) *Annals Oncol.* 8:139-146; Kuzel et al. (1993) *Leukemia Lymphoma* 11:369-377; Moreland et al. (1995) *Arthritis Rheum* 38:1177-1186; and LeMaistre et al. (1993) *Cancer Res.* 53:3930-3934), each of which are specifically incorporated by reference in their entirety.

In one embodiment the DC-targeted cell-depleting agent is an immunotoxin. As used herein, an "immunotoxin" is an antibody or antigen-binding portion thereof that is conjugated to a toxin. Accordingly, in one embodiment the immunotoxin is a DC-specific antibody or antigen-binding portion thereof that is conjugated to a toxin that is capable of killing DCs.

Toxins and immunotoxins according to the invention can be generated using recombinant DNA methodology, or they can be obtained biochemically. When the toxin is obtained using recombinant DNA methodology, DNA encoding the toxin is cloned into a suitable vector, the vector is transfected into a suitable host cell, and the toxin is generated in the host cell following transcription and translation of the DNA. Preferably, for the purposes of the present invention, DNA encoding the toxin is cloned in frame with DNA encoding an antibody or antigen-binding antibody fragment, which antibody or antigen-binding fragment thereof is specific for a DC surface molecule. Thus, the chimeric toxin molecule so generated is specific for a DC, targets the DC, binds thereto, and in some manner, effects impairment of or kills the DC.

Examples of toxins which are conjugated to an antibody or receptor molecule include the *Pseudomonas* A toxin. While the invention should in no way be construed to be limited to the use of this particular toxin, examples of chimeric molecules which include this toxin are provided in the following references to exemplify one embodiment of the invention. Essand et al. (1998) *Internatl. J. Cancer* 77:123-127; Kreitman et al. (1997) *Blood* 90:252-259; Mansfield et al. (1997) *Blood* 90:2020-2026; Maurer-Gebhard et al. (1998) *Cancer Res.* 58:2661-2666; Spyridonidis et al. (1998) *Blood* 91:1820-1827; Bera et al. (1998) *Mol Med* 4:384-391; Francisco et al. (1998) *Leukemia Lymphoma* 30:237-245; Kreitman et al. (1998) *Advanced Drug Delivery Reviews* 31:53-88; Wu (1997) *Brit. J. Cancer* 75:1347-1355; and Zdanovsky et al. (1997) *FASEB J.* 11:A1325-A1325.

DC depletion can also be accomplished by selectively introducing a nucleic acid molecule into the DC, the expression of which nucleic acid either directly results in DC cell death or renders the DC specifically susceptible to other pharmacological agents. In vivo or ex vivo depletion of DCs according to this method may be accomplished by delivering the desired nucleic acid to the DC using a viral gene delivery systems such as, but not limited to a retrovirus, adenovirus, or an adeno-associated virus gene delivery system. The desired viral delivery system may comprise a virus whose genome encodes a protein which, for example, directly causes cell death, for example by inducing apoptosis of the DC. Alternatively, the viral delivery system can contain a virus whose genome encodes, for example, a herpes simplex virus thymidine kinase gene. Expression of the herpes simplex virus thymidine kinase gene in the DC renders the DC sensitive to pharmacologic doses of ganciclovir. Thus, subsequent contact of the virally transduced DC with ganciclovir results in death of the DC.

Other genes useful for this purpose include, but are not limited to, constitutively active forms of caspases 3, 8, and 9, bax, granzyme, diphtheria toxin, *Pseudomonas* A toxin, ricin, and other toxin genes disclosed elsewhere herein. The generation of appropriate constructs for delivery of such genes to a human will be readily apparent to the skilled artisan and is described, for example, in Sambrook et al. (1989) *Molecular Cloning: A Laboratory Manual*, Cold Spring Harbor Laboratory, New York and in Ausubel et al. (1997) *Current Protocols in Molecular Biology*, John Wiley & Sons, New York.

It is important that the gene which is transferred into the cells, for the purpose of killing the cells, be placed under the control of the appropriate promoter sequence, such that induction of expression of the gene can be effected upon addition to the cells (administration to the mammal) of the appropriate inducer. Such inducible promoter sequences include, but are not limited to, promoters which are induced upon addition of a metal to the cells, steroid inducible promoters, and the like. In one embodiment, the ecdysone promoter system can be employed. In this embodiment, the ecdysone promoter is cloned upstream of the ecdysone receptor protein sequence, which is positioned upstream of a second promoter sequence which drives expression of the ecdysone binding site operably linked to the desired gene, for example, the desired toxin. Induction of the promoter induces expression of the toxin, thereby effecting killing of the cell in which the toxin gene resides.

As used herein, the term "promoter/regulatory sequence" means a nucleic acid sequence which is required for expression of a gene product operably linked to the promoter/regulator sequence. In some instances, this sequence can be the core promoter sequence and in other instances, this sequence can also include an enhancer sequence and other regulatory elements which are required for expression of the gene product. The promoter/regulatory sequence can, for example, be one which expresses the gene product in a tissue-specific manner.

Two polynucleotides can be described as "operably linked" when a single-stranded or double-stranded nucleic acid moiety includes the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As noted above, DCs can also be inhibited by antisense and RNAi mechanisms. Thus, the invention embraces antisense oligonucleotides that selectively bind to nucleic acid molecules encoding a critical protein or cytokine to decrease expression and activity of this protein and subunits thereof.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. Antisense molecules are designed so as to interfere with transcription or translation of a target gene upon hybridization with the target gene or transcript. Antisense oligonucleotides that selectively bind to a nucleic acid molecule encoding a critical protein or a cytokine such as TGF-$\beta$1 are particularly preferred. Those skilled in the art will recognize that the exact length of the antisense oligonucleotide and its degree of complementarity with its target will depend upon the specific target selected, including the sequence of the target and the particular bases which comprise that sequence.

It is preferred that the antisense oligonucleotide be constructed and arranged so as to bind selectively with the target under physiological conditions, i.e., to hybridize substantially more to the target sequence than to any other sequence in the target cell under physiological conditions. Based upon the nucleotide sequences of nucleic acid molecules encoding a target protein cytokine or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least about 10 and, more preferably, at least about 15 consecutive bases which are complementary to the target, although in certain cases modified oligonucleotides as short as 7 bases in length have been used successfully as antisense oligonucleotides. See Wagner et al. (1995) *Nat. Med.* 1:1116-1118. Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted by antisense oligonucleotides. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al. (1994) *Cell Mol. Neurobiol.* 14:439-457) and at which proteins are not expected to bind.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acid molecules has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose.

The present invention, thus, contemplates pharmaceutical preparations containing modified antisense molecules that are complementary to and hybridizable with, under physiological conditions, nucleic acid molecules encoding a critical protein or cytokine, together with pharmaceutically acceptable carriers. Antisense oligonucleotides may be administered as part of a pharmaceutical composition. In this latter embodiment, it may be preferable that a slow intravenous administration be used. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a subject.

The methods of the invention also encompass use of isolated short RNA that directs the sequence-specific degradation of a critical protein or cytokine mRNA through a process known as RNA interference (RNAi). The process is known to occur in a wide variety of organisms, including embryos of mammals and other vertebrates. It has been demonstrated that double-stranded RNA (dsRNA) is processed to RNA segments 21-23 nucleotides (nt) in length, and furthermore, that they mediate RNA interference in the absence of longer dsRNA. Thus, these 21-23 nt fragments are sequence-specific mediators of RNA degradation and are referred to herein as siRNA or RNAi. Methods of the invention encompass the use of these fragments (or recombinantly produced or chemically synthesized oligonucleotides of the same or similar nature) to enable the targeting of critical protein or cytokine mRNAs for degradation in mammalian cells useful in the therapeutic applications discussed herein.

The methods for design of the RNAs that mediate RNAi and the methods for transfection of the RNAs into cells and animals is well known in the art and are readily commercially available. Verma et al. (2004) *J. Clin. Pharm. Ther.* 28:395-404; Mello et al. (2004) *Nature* 431:338-42; Dykxhoorn et al. (2003) *Nat. Rev. Mol. Cell. Biol.* 4:457-67. Commercial suppliers of RNAi products include Proligo (Hamburg, Germany), Dharmacon Research (Lafayette, Colo.), Pierce Chemical (Rockford, Ill.), Glen Research (Sterling, Vir.), ChemGenes (Ashland, Mass.), and Cruachem (Glasgow, UK). The RNAs are preferably chemically synthesized using appropriately protected ribonucleoside phosphoramidites and a conventional DNA/RNA synthesizer. Most conveniently, siRNAs are obtained from commercial RNA oligo synthesis suppliers listed herein. In general, RNAs are not difficult to synthesize and are readily provided in a quality suitable for RNAi. A typical 0.2 µmol-scale RNA synthesis provides about 1 milligram of RNA, which is sufficient for 1000 transfection experiments using a 24-well tissue culture plate format.

The critical protein or cytokine cDNA-specific siRNA is designed preferably by selecting a sequence that is not within 50-100 bp of the start codon and the termination codon, avoids intron regions, avoids stretches of 4 or more bases such as AAAA, CCCC, avoids regions with GC content <30% or >60%, avoids repeats and low complex sequence, and it avoids single nucleotide polymorphism sites. The critical protein or cytokine siRNA may be designed by a search for a 23-nt sequence motif AA(N19). If no suitable sequence is found, then a 23-nt sequence motif NA(N21) may be used with conversion of the 3' end of the sense siRNA to TT. Alternatively, the critical protein or cytokine siRNA can be designed by a search for NAR(N17)YNN. The target sequence may have a GC content of around 50%. The siRNA targeted sequence may be further evaluated using a BLAST homology search to avoid off target effects on other genes or sequences. Negative controls are designed by scrambling targeted siRNA sequences. The control RNA preferably has the same length and nucleotide composition as the siRNA but has at least 4-5 bases mismatched to the siRNA. The RNA molecules of the present invention can comprise a 3' hydroxyl group. The RNA molecules can be single-stranded or double stranded; such molecules can be blunt-ended or comprise overhanging ends (e.g., 5', 3') from about 1 to about 6 nucleotides in length (e.g., pyrimidine nucleotides, purine nucleotides). In order to further enhance the stability of the RNA of the present invention, the 3' overhangs can be stabilized against degradation. The RNA can be stabilized by including purine nucleotides, such as adenosine or guanosine nucleotides. Alternatively, substitution of pyrimidine nucleotides by modified analogues, e.g., substitution of uridine 2 nucleotide 3' overhangs by 2'-deoxythymidine is tolerated and does not affect the efficiency of RNAi. The absence of a 2' hydroxyl significantly enhances the nuclease resistance of the overhang in tissue culture medium.

The RNA molecules used in the methods of the present invention can be obtained using a number of techniques known to those of skill in the art. For example, the RNA can be chemically synthesized or recombinantly produced using methods known in the art. Such methods are described in U.S. Published Patent Application Nos. US 2002-0086356A1 and US 2003-0206884A1 that are hereby incorporated by reference in their entirety.

The methods described herein are used to identify or obtain RNA molecules that are useful as sequence-specific mediators of critical protein or cytokine mRNA degradation and, thus, for inhibiting critical protein or cytokine activity. Expression of critical protein or cytokine can be inhibited in humans in order to prevent the protein from being translated and thus contributing to the ischemia-reperfusion injury.

The RNA molecules may also be isolated using a number of techniques known to those of skill in the art. For example, gel electrophoresis can be used to separate RNAs from the combination, gel slices comprising the RNA sequences removed and RNAs eluted from the gel slices. Alternatively, non-denaturing methods, such as non-denaturing column chromatography, can be used to isolate the RNA produced. In addition, chromatography (e.g., size exclusion chromatography), glycerol gradient centrifugation, affinity purification with antibody can be used to isolate RNAs.

Any RNA can be used in the methods of the present invention, provided that it has sufficient homology to the critical protein or cytokine gene to mediate RNAi. The RNA for use in the present invention can correspond to the entire critical protein or cytokine gene or a portion thereof. There is no upper limit on the length of the RNA that can be used. For example, the RNA can range from about 21 base pairs (bp) of the gene to the full length of the gene or more. In one embodiment, the RNA used in the methods of the present invention is about 1000 bp in length. In another embodiment, the RNA is about 500 bp in length. In yet another embodiment, the RNA is about 22 bp in length. In certain embodiments the preferred length of the RNA of the invention is 21 to 23 nucleotides.

The use of viral and non-viral vectors for delivery of genes to dendritic cells is contemplated in the invention. Viral vectors include, but are not limited to, retroviral, adenoviral, herpesviral, and other viral vectors which are well known in the art and are described, for example, in Sambrook et al. (1989) *Molecular Cloning: A Laboratory Manual*, Cold Spring Harbor Laboratory, New York and in Ausubel et al. (1997) *Current Protocols in Molecular Biology*, John Wiley & Sons, New York. It is important of course, that any viral vector delivery system used employ a virus which is replication incompetent. As stated, non-viral vectors such as liposomes and the like, can also be used to deliver a DC-depleting or -inhibiting composition to a subject.

Cells which have transduced therein a gene for cell killing, when such cells are transduced in an ex vivo manner, can be selected (i.e., separated from cells which do not comprise the gene) by providing the cells with a selectable marker in addition to the transduced gene. Selectable markers are well know in the art and are described, for example, in Sambrook et al. (1989) *Molecular Cloning: A Laboratory Manual*, Cold Spring Harbor, N.Y.).

DC depletion can further be accomplished by introducing into a population of DCs an oligonucleotide (including, but not limited to, a suitable antisense molecule, short hairpin RNA (shRNA), or small interfering RNA (siRNA)) or a ribozyme, which oligonucleotide or ribozyme is capable of inducing death of the DC, or of inducing impairment of DC function. Such oligonucleotides include those which target an essential function of a DC, defined herein as being one which either kills a DC or impairs the function of the DC with respect to stimulation of T cells. Such functions of a DC include, but are not limited to, the costimulatory function of B71, B72, and CD40, among others. Thus, oligonucleotides and ribozymes which are useful in the methods of the invention include, but are not limited to, those which are directed against these targets.

The invention in one embodiment entails administering to a subject having a post-ischemic wound a dendritic cell (DC)-targeted bone morphogenetic protein 7 (BMP7) agonist in an amount effective to increase BMP7 release by DCs in the post-ischemic wound. BMP7, which is also known as osteogenic protein 1 or OP-1, is a member of the TGF-β superfamily of proteins. BMP7 plays a key role in the transformation of mesenchymal cells into bone and cartilage. It is inhibited by noggin and a similar protein, chordin, which are expressed in the Spemann-Mangold Organizer. BMP7 may be involved in bone homeostasis. It is expressed in the brain, kidneys and bladder. BMP7 induces the phosphorylation of SMAD1 and SMAD5, which in turn induce transcription of numerous osteogenic genes. Itoh et al. (2001) *EMBO J.* 20:4132-42.

A cDNA sequence for human BMP7 is available as GenBank accession no. NM_001719, and a corresponding amino acid sequence is available as GenBank accession no. NP_001710.

A cDNA sequence for murine BMP7 is available as GenBank accession no. NM_007557, and a corresponding amino acid sequence is available as GenBank accession no. NP_031583.

Zeisberg et al. (2007) *Nature Med.* 13:952-961 showed that cardiac fibrosis is associated with the emergence of fibroblasts originating from endothelial cells, suggesting an endothelial-mesenchymal transition (EndMT) similar to events that occur during formation of the atrioventricular cushion in the embryonic heart. TGF-β1 induced endothelial cells to undergo EndMT, whereas BMP7 preserved the endothelial phenotype. The systemic administration of recombinant human BMP7 significantly inhibited EndMT and the progression of cardiac fibrosis in mouse models of pressure overload and chronic allograft rejection. Zeisberg et al. concluded that EndMT contributes to the progression of cardiac fibrosis and that recombinant human BMP7 can be used to inhibit EndMT and to intervene in the progression of chronic heart disease associated with fibrosis.

As used herein, a "BMP7 agonist" is any agent that is capable of increasing the amount or activity of BMP7 in a cell. In one embodiment a BMP7 agonist is any agent that is capable of increasing the amount or activity of BMP7 in a cell sufficient to inhibit TGF-β1 in the cell. A BMP7 agonist can include a BMP7 polypeptide, an enzymatically active fragment of a BMP7 polypeptide, a BMP7 fusion protein, a polynucleotide that encodes a BMP7 polypeptide, a polynucleotide that encodes an enzymatically active fragment of a BMP7 polypeptide, a poly nucleotide that encodes a BMP7 fusion protein, and a polynucleotide that can direct the expression of a native gene encoding BMP7.

The administering can be by any suitable route to bring the DC-targeted BMP7 agonist into contact with DCs. Administering generally includes intravascular administering. For example, in one embodiment the administering can be systemic by intravenous administration. Systemic administration of the DC-targeted BMP7 agonist will increase BMP7 release by circulating DCs as well as interstitial DCs, that is, DCs wherever they exist in the body. Accordingly, systemic administration of the DC-targeted BMP7 agonist will effect both generalized modulation of DCs as well as modulation of DCs in the post-ischemic wound. Such systemic administration can accomplished by one or more bolus injections, or by infusion, or by any combination thereof.

Alternatively or in addition to systemic administration, in one embodiment the DC-targeted BMP7 agonist is administered locally, for example by intracoronary injection, myocardial injection, pericardial injection, epicardial injection, or retrovenous injection. Local administration of the DC-targeted BMP7 agonist will preferentially affect interstitial DCs, that is, DCs in the post-ischemic wound. Such local administration can accomplished by one or more bolus injections, or by infusion, or by any combination thereof.

The administering, whether local, systemic, or a combination of local and systemic, will generally be short-term, i.e., for a duration sufficient to effect DC modulation for one to fourteen days. In various embodiments the administering will be for a duration sufficient to effect DC modulation for 1, 2, 3, 4, 5, 6, 7, 8, 9, 10, 11, 12, 13, or 14 days. In one embodiment the administering will be for a duration sufficient to effect DC modulation for up to 30 days. The invention also contemplates longer periods of administration and longer periods of DC modulation, as well as and including intermittent periods of administration and periods of DC modulation.

In one embodiment a DC-targeted BMP7 agonist is administered to a subject in conjunction with administering to the subject a DC-targeted cell-depleting agent.

The invention in one embodiment entails administering to a subject having a post-ischemic wound a dendritic cell (DC)-targeted transforming growth factor beta 1 (TGF-β1) antagonist in an amount effective to reduce TGF-β1 release by DCs in the post-ischemic wound. TGF-β1 is a polypeptide member of the transforming growth factor beta superfamily of cytokines. It is a secreted protein that performs many cellular functions, including the control of cell growth, cell proliferation, cell differentiation, and apoptosis. TGF-β1 was first identified in human platelets as a protein with a molecular mass of 25 kDa with a potential role in wound healing. Assoian et al. (1983) *J Biol Chem* 258:7155-60. It was later characterized as a large protein precursor (containing 390 amino acids) that was proteolytically processed to produce a mature peptide of 112 amino acids. Derynck et al. (1985) *Nature* 316:701-5. TGF-β1 plays an important role in controlling the immune system and shows different activities on different types of cells, or cells at different developmental stages. Most immune cells secrete TGF-β1. Letterio et al. (1998) *Annu Rev Immunol* 16:137-61.

A cDNA sequence for full-length human TGF-β1 is available as GenBank accession no. NM_000660, and a corresponding amino acid sequence (390 amino acids) is available as GenBank accession no. NP_000651.

A cDNA sequence for full-length murine TGF-β1 is available as GenBank accession no. NM_011577, and a corresponding amino acid sequence (390 amino acids) is available as GenBank accession no. NP_035707.

As used herein, a "TGF-β1 antagonist" is any agent that is capable of decreasing the amount or activity of TGF-β1 in a cell. A TGF-β1 antagonist can include a dominant negative TGF-β1 polypeptide, a polynucleotide that encodes a TGF-β1 dominant negative polypeptide, and a polynucleotide that can reduce the expression of a native gene encoding TGF-β1. A polynucleotide that can reduce the expression of a native gene encoding TGF-β1 specifically can include, without limitation, a suitable antisense polynucleotide, shRNA, or siRNA.

The administering can be by any suitable route to bring the DC-targeted TGF-β1 antagonist into contact with DCs.

Administering generally includes intravascular administering. For example, in one embodiment the administering can be systemic by intravenous administration. Systemic administration of the DC-targeted TGF-β1 antagonist will reduce TGF-β1 release by circulating DCs as well as interstitial DCs, that is, DCs wherever they exist in the body. Accordingly, systemic administration of the DC-targeted TGF-β1 antagonist will effect both generalized modulation of DCs as well as modulation of DCs in the post-ischemic wound. Such systemic administration can accomplished by one or more bolus injections, or by infusion, or by any combination thereof.

Alternatively or in addition to systemic administration, in one embodiment the DC-targeted TGF-β1 antagonist is administered locally, for example by intracoronary injection, myocardial injection, pericardial injection, epicardial injection, or retrovenous injection. Local administration of the DC-targeted TGF-β1 antagonist will preferentially affect interstitial DCs, that is, DCs in the post-ischemic wound. Such local administration can accomplished by one or more bolus injections, or by infusion, or by any combination thereof.

The administering, whether local, systemic, or a combination of local and systemic, will generally be short-term, i.e., for a duration sufficient to effect DC modulation for one to fourteen days. In various embodiments the administering will be for a duration sufficient to effect DC modulation for 1, 2, 3, 4, 5, 6, 7, 8, 9, 10, 11, 12, 13, or 14 days. In one embodiment the administering will be for a duration sufficient to effect DC modulation for up to 30 days. The invention also contemplates longer periods of administration and longer periods of DC modulation, as well as and including intermittent periods of administration and periods of DC modulation.

In one embodiment a DC-targeted TGF-β1 antagonist is administered to a subject in conjunction with administering to the subject a DC-targeted cell-depleting agent.

In one embodiment a DC-targeted TGF-β1 antagonist is administered to a subject in conjunction with administering to the subject a DC-targeted BMP7 agonist.

In one embodiment a DC-targeted TGF-β1 antagonist is administered to a subject in conjunction with administering to the subject a DC-targeted cell-depleting agent and a DC-targeted BMP7 agonist.

For clinical use, a DC-targeted agent of the invention can be administered any time within six months after an ischemic event. In one embodiment the agent is first administered within six hours of the onset of the ischemic event. In various embodiments the agent is first administered within 1, 2, 3, 4, 5, 6, or 7 days from the onset of the ischemic event. In one embodiment the agent is first administered within 2 weeks of the onset of the ischemic event. In one embodiment the agent is administered only once. In one embodiment the agent is administered more than once.

Any particular DC-targeted agent of the invention can be used in combination with at least one other DC-targeted agent of the invention. Such use in combination can be at the same time or at different times.

The agent can be administered in conjunction with any other therapy suitable for treatment of the condition of the subject. For example, the agent can be administered in conjunction with cardiac catheterization and coronary artery angioplasty in a subject having an acute myocardial infarction.

The invention further provides pharmaceutical compositions. The pharmaceutical compositions of the invention include at least one DC-targeted cell-depleting agent of the invention, at least one DC-targeted BMP7 agonist of the invention, at least one DC-targeted TGF-β1 antagonist of the invention, or any combination thereof, in a pharmaceutically acceptable carrier.

The invention further provides a method of preparing pharmaceutical compositions of the invention. The method includes the step of placing at least one DC-targeted cell-depleting agent of the invention, at least one DC-targeted BMP7 agonist of the invention, at least one DC-targeted TGF-β1 antagonist of the invention, or any combination thereof, in a pharmaceutically acceptable carrier.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is effective to treat the particular subject. The effective amount for any particular application can vary depending on such factors as the disease or condition being treated, the particular DC-targeted agent of the invention being administered, the size of the subject, or the severity of the disease or condition. One of ordinary skill in the art can empirically determine the effective amount of a particular DC-targeted agent of the invention and/or other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug. "Dose" and "dosage" are used interchangeably herein.

Generally, daily doses of active compounds will be from about 0.1 milligrams/kg body weight per day to 100 milligrams/kg body weight per day. It is expected that doses in the range of 0.5 to 50 milligrams/kg body weight, in one or several administrations per day, will yield the desired results. Dosage may be adjusted appropriately to achieve desired drug levels, local or systemic, depending upon the mode of administration. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of compounds.

For any compound described herein the therapeutically effective amount can be initially determined from animal models. A therapeutically effective dose can also be determined from human data for DC-targeted agent of the inventions which have been tested in humans and for compounds which are known to exhibit similar pharmacological activities, such as other related DC-targeted agent of the inventions. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the DC-targeted agent of the invention can be administered to a subject by any mode that delivers the DC-targeted agent of the invention to the desired surface. Administering the pharmaceutical composition of the present invention can be accomplished by any means known to the skilled artisan. Routes of administration include but are not limited to intravenous, intra-arterial, and intracoronary.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds can be in powder form for constitution with a suitable vehicle, e.g., sterile pyrogen-free water, before use.

The DC-targeted agent of the inventions and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of a DC-targeted agent of the invention and optionally therapeutic agents included in a pharmaceutically-acceptable carrier. The term "pharmaceutically-acceptable carrier" means one or more compatible solid or liquid fillers, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The present invention is further illustrated by the following examples, which in no way should be construed as further limiting. The entire contents of all of the references (including literature references, issued patents, published patent applications, and co-pending patent applications) cited throughout this application are hereby expressly incorporated by reference.

EXAMPLES

Mouse Model of Myocardial Infarction

To study the effect of temporary depletion of $CD11c^+$ DC on wound healing after myocardial infarction (MI), diphtheria toxin receptor (DTR) transgenic mice and their wild type littermates were used. Wild type mice are naturally resistant to diphtheria toxin (DT) because they do not express DTR. DTR transgenic mice carry a simian DTR-GFP (green fluorescent protein) fusion protein under control of the CD11c promoter, resulting in murine DTR expression restricted to the DC compartment while other cells remain resistant to DT because of their low affinity to DT. Jung et al. (2002) *Immunity.* 17:211-220.

Mice were anesthetized with a 0.05 ml intra-peritoneal (i.p.) injection of ketamine/xylazine at 100 mg ketamine and 13 mg xylazine in 25 ml, intubated, connected to a ventilator (MiniVent, Hugo Sachs Elektronik, March-Hugstetten, Germany), and anesthesia was maintained with isofluorane 2% in oxygen. The electrocardiogram was monitored with a sinus rhythm analyzer (Transoma Medical Inc, St Paul, Minn.) connected to an analysis software package (Digimed Innovation, Laval, Quebec, Canada). A left lateral thoracotomy was performed, the left anterior descending coronary artery (LAD) was ligated at 3 mm below the left atrial appendage. Coronary artery occlusion was confirmed by ST-segment elevation on the electrocardiogram. Sham-operated mice underwent the same procedure except the LAD was not ligated.

Echocardiography. Seven days after induction of myocardial infarction, the animals were re-anesthetized with isofluorane 2% in oxygen and echocardiograms were obtained with a high frequency ultrasound scanner (Vevo 770, Visualsonics, Toronto, Ontario, Canada). Myocardial infarct size was measured by defining the maximal extent of the abnormally moving segment along the long axis long axis followed by determination of the maximal extent of abnormal wall motion in the short axis view. For the latter purpose the short axis view was divided into twelve equal segments in clockwise fashion and the percentage of short-axis involvement was calculated by dividing the number of abnormal segments by the number 12 (e.g., $4/12 \times 100\% = 33\%$). The total percentage of infarction was calculated by multiplying the percentage of long-axis involvement by the short-axis percentage.

Tissue Processing. After acquisition of the physiologic measurements in vivo, the animals were euthanized through exsanguination under isofluorane anesthesia and residual blood was removed from the vasculature by perfusion with heparinized normal saline at 100 mmHg for a period of three minutes. Subsequently, the infarcted and non-infarcted areas of the heart were separated placing the incision 1 mm from the infarct border zone in the viable segment to avoid contamination of viable tissue with cells from hibernating or non-viable myocardial segments.

Cell isolation, quantification and characterization. Cells were isolated mechanically from the viable and infarcted segments of the hearts. After staining with the appropriate antibodies, they were quantified and characterized by fluorescence-activated cell sorting (FACS) analysis.

Immunohistochemistry. Three serial sections at 4 μm thickness were taken at 250 μm intervals throughout the viable and infarcted heart segments. The tissue was stained with antibodies against the endothelial markers CD31, von Willebrand factor, and lectin in combination with the pan-leukocyte marker CD45. Alternatively or in addition, cells or tissue can be stained with antibodies against an apoptosis marker, e.g., annexin-V. Immunostaining was performed according to conventional methods with biotin- or FITC (anti-smooth muscle actin)—labeled secondary antibodies and 3,3'-diaminobenzidine (DAB) as a chromogen. Sections were counterstained with hematoxylin and mounted with coverslips. In all immunohistochemistry, sections treated without the respective primary antibody served as controls.

Morphometry. To assess MI size by morphometry, the left ventricle (LV) was sectioned serially into 300 µm slices which were stained with 2,3,5-triphenyltetrazolium chloride (TTC). The TTC positive area and total LV area were measured by Image-J, and MI-size was expressed as % area of the total LV area.

RNA Isolation and Reverse Transcriptase Polymerase Chain Reaction. The viable and infarcted segments of the hearts were placed in RNAlater (Qiagen Inc., Valencia, Calif.). After isolation of RNA, expression of PR39 was assayed by reverse transcriptase polymerase chain reaction (RT-PCR).

Example 1

Anti-DC Immunotoxins for Use in Mice and Humans

A PE38-based anti-VLC immunotoxin to target DC in mice was prepared using a truncated mutant of *Pseudomonas aeruginosa* exotoxin A (PE38) that has exhibited great safety in clinical trials. Kreitman et al. (2005) *J. Clin. Oncol.* 23:6719-29. The two variable chains ($V_H$ and $V_L$) of the anti-CD11c hybridoma N418 (ATCC #HB-224). The sequences were then connected in frame by a fragment encoding for a peptide linker, as described. Demangel et al. (2005) *Mol. Immunol.* 42:979-985. Next, this anti-CD11c scFv was subcloned in frame with the hinge sequence of CD8, followed by PE38 (ATCC #67205). The exotoxin encoded by this sequence lacks the cell-binding domain, so the protein is harmless in the absence of a recognition sequence. However, the single-chain antibody in the resulting fusion gene binds to CD11c. It is therefore internalized by CD11c$^+$ cells, bringing the lethal activity to the cytosol of VLCs. Kreitman et al. (2005) *J. Clin. Oncol.* 23:6719-29.

This fusion gene was subcloned into a pET-28a(+) plasmid (Novagen) for expression in *E. coli* BL21 (DE3; Invitrogen). To produce immunotoxin, recombinant bacteria were harvested 15 h after induction of recombinant protein expression with 1 mM IPTG. As expected, the proteins accumulated in inclusion bodies. Optimum conditions of denaturation, refolding and dialysis have been previously published. FitzGerald et al. (2004) *Int. J. Med. Microbiol.* 293:577-582; Brinkmann et al. (1991) *Proc. Natl. Acad. Sci. USA.* 88:8616-8620. A final amount of ca. 1 mg of depyrogenated, purified immunotoxin was obtained. Reed et al. (2003) *J. Biol. Chem.* 278:31853-31860.

To target the immunotoxin to human DC, the anti-CD11c recognition sequence is replaced by anti-DEC205.

Example 2

Appearance of Vascular Leukocytes Following Myocardial Infarction

In a time course experiment of MI in wild type mice, vascular leukocytes (VLC), i.e. cells that express both leukocyte and endothelial markers, appeared in the viable segment of the hearts as early as two days after induction of MI. At four days after MI these cells are located in the vessels of the healing infarct wound, and they remain present in these vessels up to 14 days after MI. At this latter time point VLC were also found in the extravascular space of the infarct area.

The resolution of light microscopy and confocal microscopy was not sufficient to determine the exact location of VLC relative to the endothelial cells of the vasculature in the healing MI wound. Electron microscopy at four days post-MI revealed that dendritic cells are located at the abluminal surface of the basement membrane in vessels of the infarct wound, in close proximity to the endothelial cells.

Figure 1B:
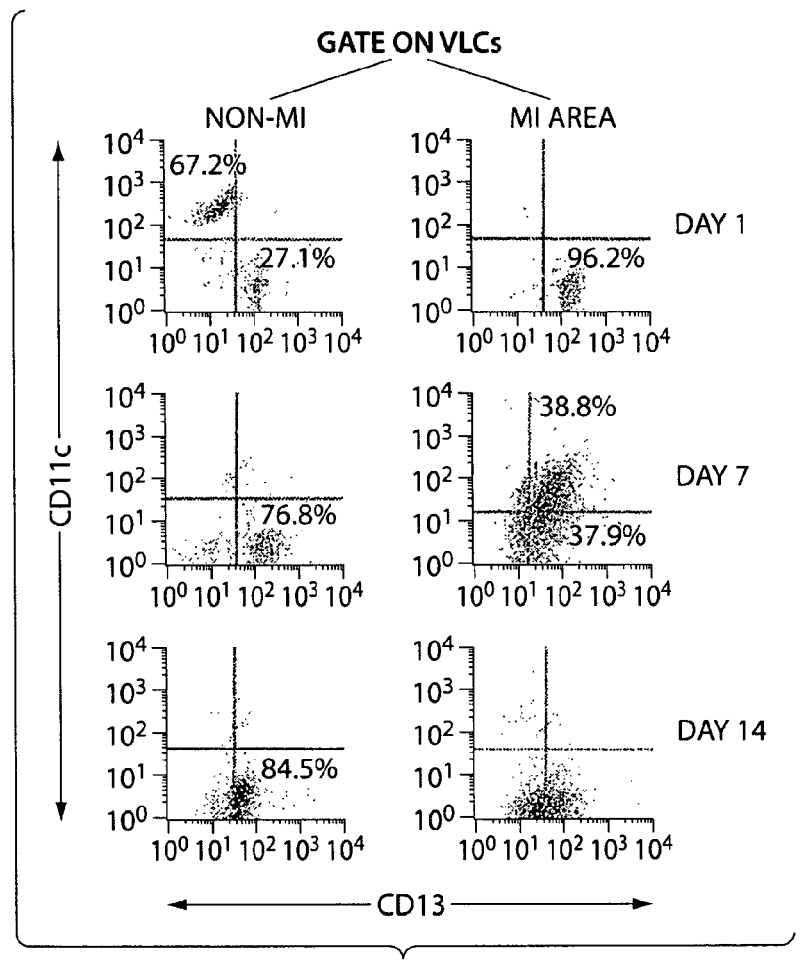
Figure 1C:
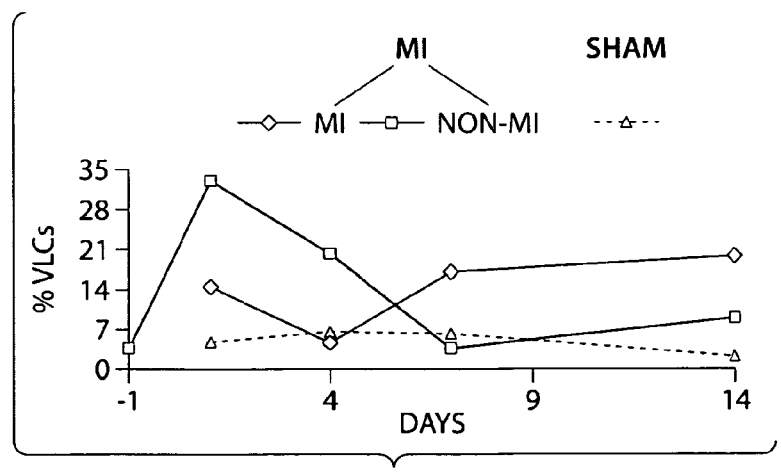

FIG. 1 summarizes the results of FACS analysis. In a time course of wound healing after MI in wild type mice, VLC first peaked in the viable segment of the infarcted heart at four days post-MI and then peaked in the infarct wound at seven days post-MI. A substantial percentage of VLC (38.8%) was positive for the myeloid marker CD13/APN and the dendritic cell marker CD11c.

Example 3

Depletion of CD11c$^+$ Dendritic Cells During Wound Healing after Myocardial Infarction Significantly Reduces Infarct Size and Preserves LV Function A single injection of DT has previously been shown to deplete DC with a nadir one to two days after injection and full recovery of DC number at seven days after injection. Jung et al. (2002) *Immunity.* 17:211-220. Transgenic DTR mice and wild type mice were randomized to injection of DT during surgery for induction of MI and physiologic readouts were acquired after MI at the time point when DC were most abundant in the MI area, i.e., seven days after MI (FIG. 1). Transgenic mice injected with phosphate buffered saline (PBS) served as controls for DT injection.

Figure 2:
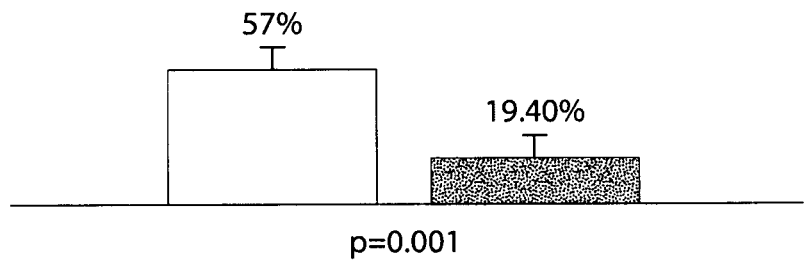
FIG. 2 is a graph depicting myocardial infarction size in diphtheria toxin (DT) receptor transgenic mice (TG), as assessed by morphometry seven days after myocardial infarction. Mice were treated with DT or phosphate-buffered saline (PBS) placebo, as indicated.
Figure 3:
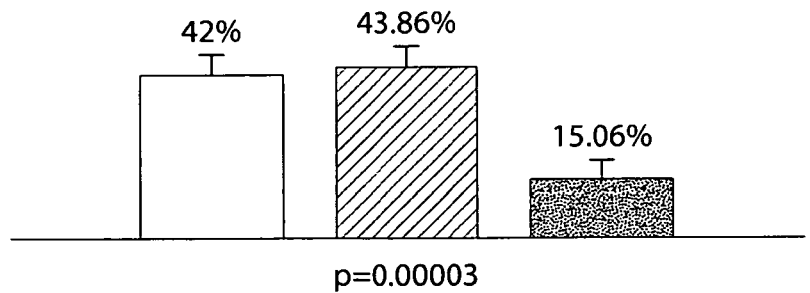
FIG. 3 is a graph depicting myocardial infarction size in diphtheria toxin (DT) receptor transgenic mice (TG) and in wild type litter mates (WT), as assessed using echocardiography seven days after myocardial infarction. Mice were treated with DT or phosphate-buffered saline (PBS) placebo, as indicated.
Figure 4:
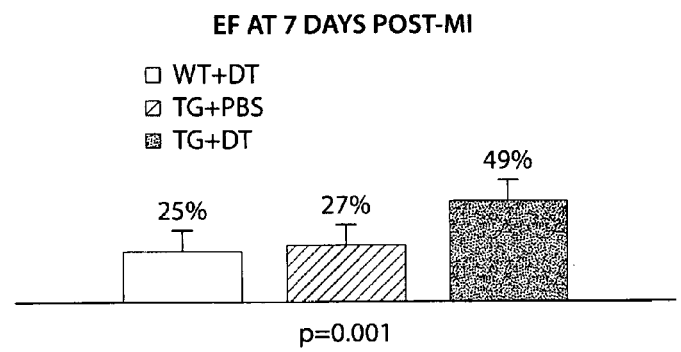
FIG. 4 is a graph depicting left ventricular ejection fraction in diphtheria toxin (DT) receptor transgenic mice (TG) and in wild type litter mates (WT), as assessed using echocardiography seven days after myocardial infarction. Mice were treated with DT or phosphate-buffered saline (PBS) placebo, as indicated.

At seven days after MI there was a significant reduction in MI size by morphometry (FIG. 2) as well as by echocardiography (FIG. 3). There was also significantly greater preservation of LV function in those animals that had received DT (FIG. 4).

Example 4

TGF-β1 Expression is Suppressed and BMP7 Expression is Increased in Viable Tissue It was previously reported that CD13/APN$^+$ endothelial cells in the MI wound express CD105, also known as endoglin, and that VLC express the endothelial marker VE-Cadherin. Buehler et al. (2006) *Arterioscler. Thromb. Vasc. Biol.* 26:2681-2687. Endoglin is a co-receptor for TGF-β1 and VE-Cadherin has been shown to be a critical regulator of TGF-β1 signaling. Rudini et al. (2008) *EMBO J.* 27:993-1004. Recently scar formation after MI has been shown to be dependent on the balance between TGF-β1 and BMP7 with TGF-β1 promoting scar formation and BMP7 achieving the opposite effect. Zeisberg et al. (2007) *Nat. Med.* 13 (8):952-961.

Figure 5:
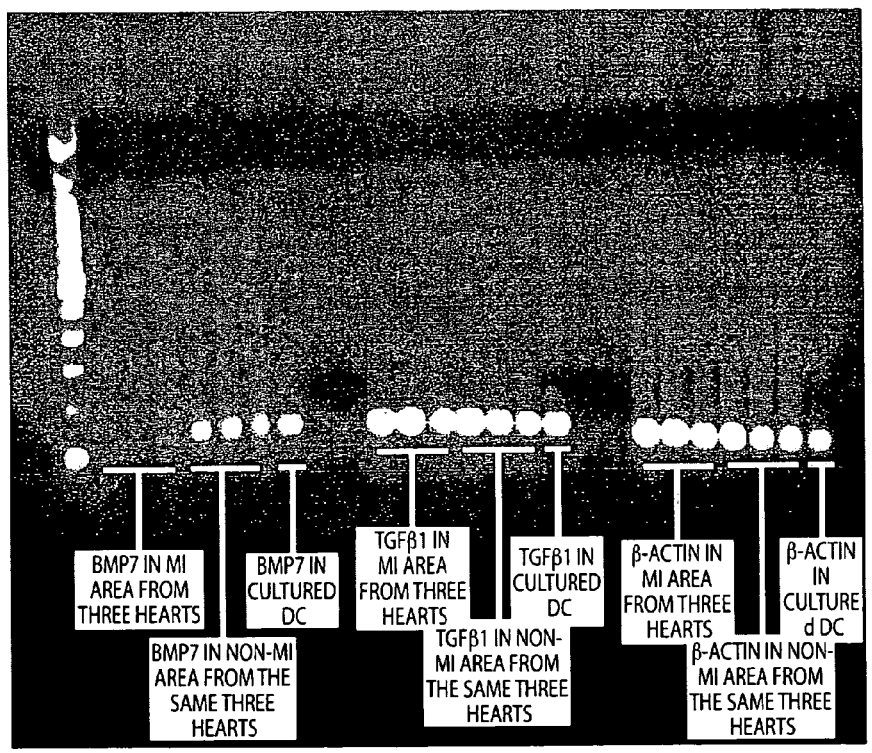
FIG. 5 is a photographic image of a gel showing that at seven days after myocardial infarction TGF-β1 expression is low in the non-infarcted segment of the heart and BMP7 is strongly expressed, whereas in the infarcted segment and in cultured dendritic cells TGF-β1 and BMP7 appear to be equally abundant. β-actin is shown as a control.

To test the hypothesis that a beneficial effect of DC depletion on MI wound healing may be brought about by modulating the balance of TGF-β1 and BMP7 production by DC and VLC, the amount of TGF-β1 and BMP7 in the viable and MI areas of wild type hearts after MI and in cultured DC were determined. At seven days after MI, in the viable segment of the heart the expression of TGF-β1 was low and BMP7 expression was high. In contrast, in the MI area as well as in cultured DC, both molecules appeared to be equally abundant (FIG. 5).

Example 5

Mouse Model of Myocardial Ischemia-Reperfusion Injury

To study the effect of temporary depletion of CD11c+ DC on wound healing after ischemia-reperfusion injury (IR) in mice, the animals are intubated and ventilated as described above and a left lateral thoracotomy is performed. A ligature is placed around the left anterior descending coronary artery (LAD) and occlusion of the LAD is confirmed by ST-segment elevation on the electrocardiogram (EKG). After 20 min the ligature is released and reperfusion is confirmed by normalization of the ST-segment. DC are depleted in wild type mice and in mice transplanted with human hematopoietic stem cells that exhibit human white blood cell lineages. Ischemia-reperfusion injury is assessed by echocardiography, tissue processing, cell quantification and characterization, immunohistochemistry, morphometry, and RT-PCR as described above.

Example 6

Porcine Model of Myocardial Ischemia-Reperfusion Injury

To study the effect of temporary depletion of CD11c+ DC on wound healing after IR in a large animal model with a coronary anatomy relevant to humans, pigs undergo balloon occlusion of the LAD for 45 min.

Anesthesia is induced with ketamine followed by intubation and ventilation with isofluorane/$O_2$. A sheath is placed in the right femoral artery and an angioplasty guide catheter is positioned at the ostium of the left coronary artery. A 0.014" guide wire is advanced into the LAD over which an angioplasty balloon is positioned in the LAD distal from the first diagonal branch. The balloon is inflated at 2-4 atm pressure for a period of 45 min, whereupon the balloon is deflated and removed.

This procedure creates a myocardial wound that is in an edematous transition stage at one week post IR and has progressed to a transmural scar at two weeks post IR.

Ischemia-reperfusion injury is assessed by echocardiography, tissue processing, cell quantification and characterization, immunohistochemistry, morphometry, and RT-PCR as described above.

Example 7

Peptide-Based Targeting of Dendritic Cells

As an alternative to antibody-based targeting of DC, peptide sequences with affinity for DC surface molecule are identified by phage display and other methods and synthesized using standard methods. These peptides are linked to immunotoxins to achieve the desired depletion of DC.

Example 8

Appearance of Dendritic Cells in Human Hearts Post MI

To determine if dendritic cells localize to the heart following an ischemic event, myocardial tissue from human patients who had recently suffered a myocardial infarction (minutes to days afterwards) were examined. After slicing tissue from various heart locations (infarct and non-infarct zones) to a thickness of 25 µm, sections were stained for the presence of mannose receptor (MR), a known surface marker of dendritic cells.

MR-positive cells were found in all heart areas, with no bias towards infarct or non-infarct areas. MR+ cells were also evenly distributed throughout the tissue. Tissue taken minutes after an ischemic event showed the same distribution of MR+ cells compared to tissue taken up to one week post trauma.

These results indicate that dendritic cells are localizing to cardiac tissue following an ischemic event.

Example 9

Localization of MR+ Dendritic Cells to Myocardium Following MI in Murine Model

We have previously shown that DC home to the MI area and CD11c+ DC were detected as early as the first day post-MI in the infarcted heart. In this example it was established that CD11c+ DC in mice also expressed the mannose receptor just as their counterparts in the human MI tissue. Hearts were excised from mice 4- and 7-days post MI surgery. Cells were isolated and incubated with the relevant antibodies and FACS analysis was used to determine the extent to which cells expressing mouse mannose receptor (mMR) were found in the cardiac tissue.

Compared to non-MI hearts, an increase in mMR+ cells was seen in both 4- and 7-day post MI myocardial tissues. Further analysis revealed that the ventricles showed a greater increase in mMR+ cells compared to the atria. This may reflect the fact that the left anterior descending artery, which supplies blood to the ventricles, is tied off during the MI surgery.

These data confirm that, just as in humans, in mice MR+ dendritic cells localize to the heart following an ischemic event.

Example 10

Appearance of Dendritic Cells in Murine CLI Model

Figure 6:
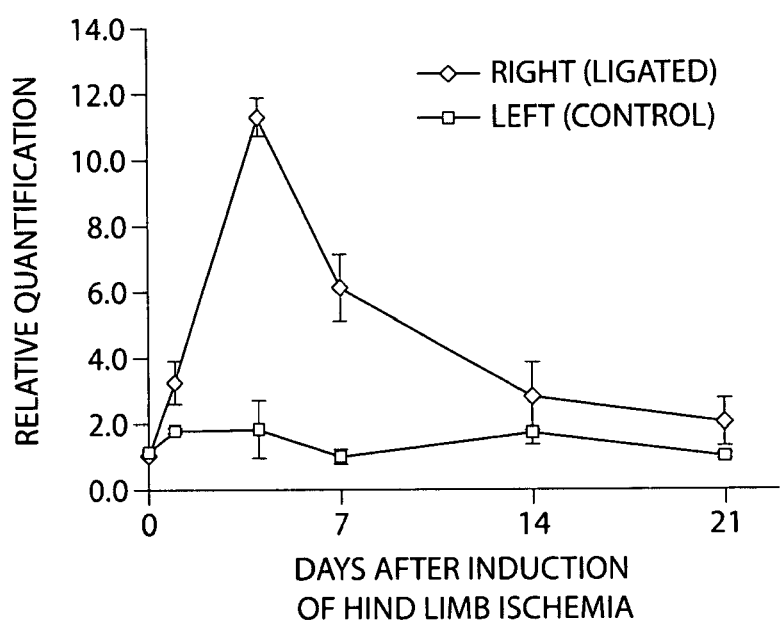
FIG. 6 is a graph depicting CD13 mRNA expression in gastrocnemius muscle of mice subjected to hind limb ischemia. mRNA levels shown are normalized to CD13 mRNA in left gastrocnemius in unoperated mouse. Error bars are ±SEM.

To determine if dendritic cells localize to the hind limb following an ischemic event, CD13 mRNA was monitored over time by RTqPCR in a mouse model designed to simulate CLI. CD13 is co-expressed with CD11c on approximately 40% of vascular leukocytes. In separate experiments CD13 expression peaked in gastrocnemius muscle at day 4 post ligation. Representative results are shown in FIG. 6. Thus both in the MI model and the CLI model, CD13 and CD11c expression localized to areas of tissue necrosis resulting from ischemia; CD13 expression is not detectable in control non-ligated limbs.

These results indicate that dendritic cells localize to the hind limb following an ischemic event.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of promoting healing of an ischemia-related cardiac tissue injury in a subject, comprising administering to a subject who has had an ischemic event and has an ischemia-related cardiac tissue injury an antibody or an antigen-binding fragment that binds to a dendritic cell (DC) surface marker in an amount effective to deplete DCs in the ischemia-related cardiac tissue injury, thereby promoting healing of the ischemia-related cardiac tissue injury, wherein the DC surface marker is selected from CD11c, CD205, CD206, and CD209.

2. The method of claim 1, wherein the DC surface marker is CD206.

3. The method of claim 1, wherein the antibody or antigen-binding fragment is conjugated to a toxin.

4. The method of claim 3, wherein the toxin is diphtheria toxin (DT), *Pseudomonas* exotoxin A (PEA), ricin, saporin, gelonin or an enzymatically active fragment thereof.

5. The method of claim 1, wherein the antibody or antigen-binding fragment is conjugated to a nanoparticle.

6. The method of claim 5, wherein the nanoparticle is coated with or encapsulates a toxin.

7. The method of claim 6, wherein the toxin is diphtheria toxin (DT), *Pseudomonas* exotoxin A (PEA), ricin, saporin, gelonin or an enzymatically active fragment thereof.

8. The method of claim 1, wherein antibody or antigen-binding fragment is conjugated to a liposome or plasma membrane vesicle.

9. The method of claim 8, wherein the liposome or plasma membrane vesicle is coated with or encapsulates a toxin.

10. The method of claim 9, wherein the toxin is diphtheria toxin (DT), *Pseudomonas* exotoxin A (PEA), ricin, saporin, gelonin or an enzymatically active fragment thereof.

11. The method of claim 1, wherein the ischemia-related cardiac tissue injury is an acute myocardial infarction.

12. The method of claim 1, wherein the subject is a human.

13. The method of claim 1, wherein the antibody or the antigen-binding fragment is first administered within seven days after the ischemic event.

14. A method of promoting healing of an ischemia-related cardiac tissue injury in a subject, comprising administering to a subject who has had an ischemic event and has an ischemia-related cardiac tissue injury an antibody or an antigen-binding fragment that binds to a dendritic cell (DC) surface marker in an amount effective to reduce tissue necrosis in the ischemia-related cardiac tissue injury, thereby promoting healing of the ischemia-related cardiac tissue injury, wherein the DC surface marker is selected from CD11c, CD205, CD206, and CD209.

15. The method of claim 14, wherein the DC surface marker is CD206.

16. The method of claim 14, wherein the antibody or antigen-binding fragment is conjugated to a toxin.

17. The method of claim 16, wherein the toxin is diphtheria toxin (DT), *Pseudomonas* exotoxin A (PEA), ricin, saporin, gelonin or an enzymatically active fragment thereof.

18. The method of claim 14, wherein the antibody or antigen-binding fragment is conjugated to a nanoparticle.

19. The method of claim 18, wherein the nanoparticle is coated with or encapsulates a toxin.

20. The method of claim 19, wherein the toxin is diphtheria toxin (DT), *Pseudomonas* exotoxin A (PEA), ricin, saporin, gelonin or an enzymatically active fragment thereof.

21. The method of claim 14, wherein the antibody or antigen-binding fragment is conjugated to a liposome or plasma membrane vesicle.

22. The method of claim 21, wherein the liposome or plasma membrane vesicle is coated with or encapsulates a toxin.

23. The method of claim 22, wherein the toxin is diphtheria toxin (DT), *Pseudomonas* exotoxin A (PEA), ricin, saporin, gelonin or an enzymatically active fragment thereof.

24. The method of claim 14, wherein the post-ischemic wound is an acute myocardial infarction.

25. The method of claim 14, wherein the subject is a human.

26. The method of claim 14, wherein the antibody or the antigen-binding fragment is first administered within seven days after the ischemic event.

* * * * *